(12) United States Patent
Chopra et al.

(10) Patent No.: US 9,422,440 B2
(45) Date of Patent: *Aug. 23, 2016

(54) BIS-UREAS AS AMORPHOUS MATERIALS FOR PHASE-CHANGE INK

(71) Applicant: XEROX CORPORATION, Norwalk, CT (US)

(72) Inventors: Naveen Chopra, Oakville (CA); Adela Goredema, Mississauga (CA); Kentaro Morimitsu, Mississauga (CA); Stephan V. Drappel, Toronto (CA); Jeffrey H. Banning, Hillsboro, OR (US)

(73) Assignee: XEROX CORPORATION, Norwalk, CT (US)

( * ) Notice: Subject to any disclaimer, the term of this patent is extended or adjusted under 35 U.S.C. 154(b) by 81 days.

This patent is subject to a terminal disclaimer.

(21) Appl. No.: 14/099,137

(22) Filed: Dec. 6, 2013

(65) Prior Publication Data

US 2015/0159033 A1    Jun. 11, 2015

(51) Int. Cl.
| | |
|---|---|
| *C07C 275/14* | (2006.01) |
| *C09D 11/322* | (2014.01) |
| *C09D 11/34* | (2014.01) |
| *C09D 11/38* | (2014.01) |

(52) U.S. Cl.
CPC ............ *C09D 11/38* (2013.01); *C07C 275/14* (2013.01); *C09D 11/322* (2013.01); *C09D 11/34* (2013.01)

(58) Field of Classification Search
None
See application file for complete search history.

(56) References Cited

U.S. PATENT DOCUMENTS

| | | |
|---|---|---|
| 5,231,135 A | 7/1993 | Machell |
| 5,621,022 A | 4/1997 | Jaeger |
| 6,221,137 B1 | 4/2001 | King |
| 6,472,523 B1 | 10/2002 | Banning |
| 6,476,219 B1 | 11/2002 | Duff |
| 6,576,747 B1 | 6/2003 | Carlini |
| 6,576,748 B1 | 6/2003 | Carlini |
| 6,590,082 B1 | 7/2003 | Banning |
| 6,646,111 B1 | 11/2003 | Carlini et al. |
| 6,663,703 B1 | 12/2003 | Wu |
| 6,673,139 B1 | 1/2004 | Wu et al. |
| 6,696,552 B2 | 2/2004 | Mayo |
| 6,713,614 B2 | 3/2004 | Carlini |

(Continued)

OTHER PUBLICATIONS

Deaton, Low Molecular Weight Bis-urea Organogelators, Feb. 21, 2002, http://www.chemistry.illinois.edu/research/organic/seminar_extracts/2001_2002/s02_Deaton.pdf, pp. 9-16.*

(Continued)

*Primary Examiner* — An Do
*Assistant Examiner* — Renee I Wilson
(74) *Attorney, Agent, or Firm* — MH2 Technology Law Group LLP

(57) ABSTRACT

An embodiment of the present disclosure is directed to an amorphous bis-urea compound having a formula 1:

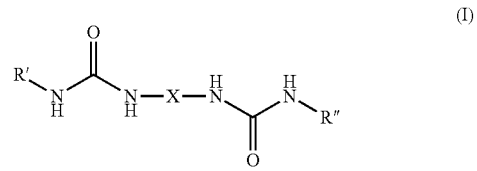

where X is a branched alkyl bridge and R' and R" are alkyl groups.

20 Claims, 3 Drawing Sheets

(56) References Cited

U.S. PATENT DOCUMENTS

| | | | |
|---|---|---|---|
| 6,726,755 B2 | 4/2004 | Titterington | |
| 6,755,902 B2 | 6/2004 | Banning | |
| 6,821,327 B2 | 11/2004 | Jaeger et al. | |
| 6,958,406 B2 | 10/2005 | Banning | |
| 7,053,227 B2 | 5/2006 | Jaeger et al. | |
| 7,220,300 B2 * | 5/2007 | Goredema | C08G 18/2825 106/31.29 |
| 7,381,831 B1 | 6/2008 | Banning | |
| 7,427,323 B1 | 9/2008 | Birau et al. | |
| 8,940,935 B2 * | 1/2015 | Chopra | C07C 275/26 564/54 |
| 2008/0267896 A1 * | 10/2008 | Feltin | A61K 8/31 424/70.1 |
| 2012/0274699 A1 | 11/2012 | Belelie et al. | |
| 2014/0285594 A1 * | 9/2014 | Morimitsu et al. | 347/88 |
| 2015/0059615 A1 * | 3/2015 | Chopra et al. | 106/31.13 |
| 2015/0103122 A1 * | 4/2015 | Chopra et al. | 347/99 |

OTHER PUBLICATIONS van Esch et al., Self-Assembly of Bis-urea Compounds in Organic Solvents and on Solid Substrates, 1997, Chem. Eur. J., 3. No. 8, pp. 1238-1243.*

Morimitsu et al. "Ink Composition and Method of Jetting Ink", U.S. Appl. No. 13/848,365, filed Mar. 21, 2013, 42 Pages.

Chopra et al. "Inks Comprising Amorphous Ureas", U.S. Appl. No. 14/018,334, filed Sep. 4, 2013, 25 Pages.

Chopra et al. "Phase Change Ink Containing Amorphous Amides", U.S. Appl. No. 14/052,865, filed Oct. 14, 2013, 60 Pages.

* cited by examiner

BIS-UREAS AS AMORPHOUS MATERIALS FOR PHASE-CHANGE INK

FIELD OF THE DISCLOSURE

The present disclosure is directed to bis-ureas as amorphous compounds for use in crystalline-amorphous inks and phase-change ink compositions containing the same.

BACKGROUND

Crystalline-amorphous inks, sometimes referred to as phase-change inks, are known as one alternative for solid ink jet printing. Some known phase-change ink designs use a mixture of crystalline and amorphous materials. The crystalline material imparts a hardness and rapid phase change that is required for DTP (direct-to-paper) print architectures. The amorphous material (typically a viscous, tacky material) aids in adhesion to the substrate and plasticizes the crystalline component to prevent embrittlement and cracking of the printed image.

Thus far, many amorphous and crystalline materials have been developed. To date, the amorphous materials have almost exclusively been comprised of esters. One known amorphous component is a derivative of L-tartaric acid/cyclohexanol/tBu cyclohexanol ("TBCT"), which is considered to contribute to acceptable robust images. However, TBCT suffers from several disadvantages, such as thermal stability during synthesis and variation in product distributions, both of which pose challenges for scale-up synthesis. Furthermore, inks containing TBCT do not meet rub resistance requirements for finishing.

Ureas are generally known in the chemical industry as the strongest hydrogen bonding materials in the functional group series of carbonates, esters, urethanes, and amides. Ureas are also known to be less prone to hydrolysis than these other compounds. Owing to the strong hydrogen bonding, ureas tend to be very viscous. For this reason, many if not most ureas would be considered unsuitable for use as inks for inkjet printing, since inkjet printing technology generally employs inks having relatively low viscosities at printer operating temperatures.

It would be considered an advancement in the art to provide novel classes of materials that are suitable for use as the amorphous component in crystalline-amorphous phase-change inks.

SUMMARY

An embodiment of the present disclosure is directed to novel amorphous compound used in phase-change ink compositions. The amorphous compound is a bis-urea of formula 1:

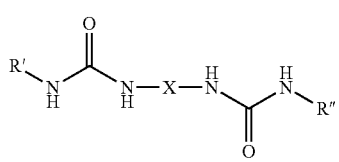

(1)

where X is a branched alkyl bridge and R' and R" are alkyl groups.

Another embodiment of the present disclosure is directed to a method. The method comprises providing an ink jet printing device including a phase change ink composition. The phase change ink composition is in solid form and comprises (a) a crystalline component, (b) an amorphous bis-urea component, and (c) optionally a colorant. The amorphous bis-urea component is a compound of formula 1, above, where X is a branched alkyl bridge and R' and R" are alkyl groups. The solid phase change ink composition is heated to a temperature above the melting point of the composition to liquefy the ink composition. The liquefied ink composition is jetted from the ink jet printing device onto a substrate to form an image.

Another embodiment of the present disclosure is directed to a phase change ink composition. The phase change ink composition comprises a crystalline component and an amorphous bis-urea component having a compound of formula 1, above, where X is a branched alkyl bridge; and R' and R" are alkyl groups. The phase change ink composition optionally comprises a colorant. The ink containing the amorphous bis-urea component has a viscosity less than 15 cps at a temperature of about 140° C.

It is to be understood that both the foregoing general description and the following detailed description are exemplary and explanatory only and are not restrictive of the present teachings, as claimed.

BRIEF DESCRIPTION OF THE DRAWINGS

The accompanying drawings, which are incorporated in and constitute a part of this specification, illustrates embodiments of the present teachings and together with the description, serve to explain the principles of the present teachings.

Figure 1:
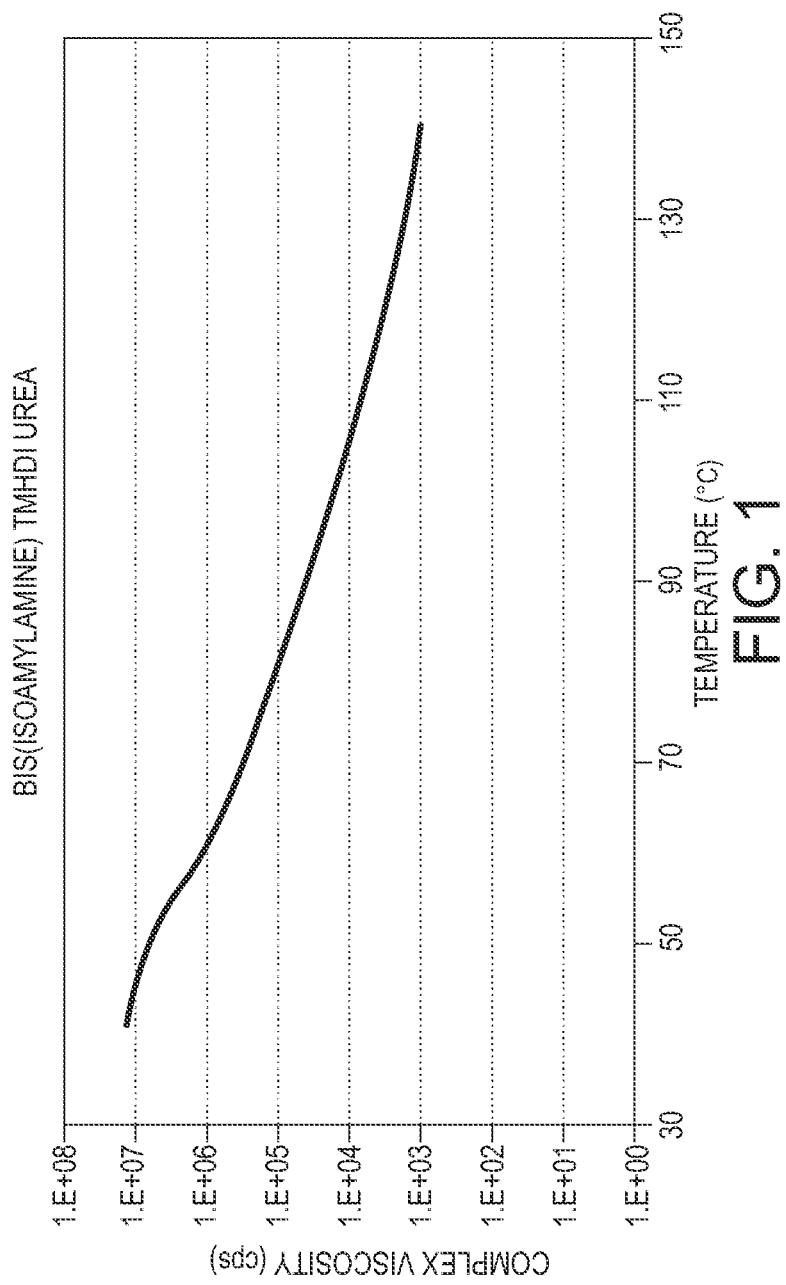
FIGS. 1 and 2 show viscosity and DSC (differential scanning calorimetry) data that was collected, according to an example of the present disclosure.

It should be noted that some details of the figure have been simplified and are drawn to facilitate understanding of the embodiments rather than to maintain strict structural accuracy, detail, and scale.

DESCRIPTION OF THE EMBODIMENTS

Reference will now be made in detail to embodiments of the present teachings, examples of which are illustrated in the accompanying drawings. In the drawings, like reference numerals have been used throughout to designate identical elements. In the following description, reference is made to the accompanying drawing that forms a part thereof, and in which is shown by way of illustration a specific exemplary embodiment in which the present teachings may be practiced. The following description is, therefore, merely exemplary.

Amorphous Component

The amorphous bis-urea components of the present disclosure are compounds of formula I:

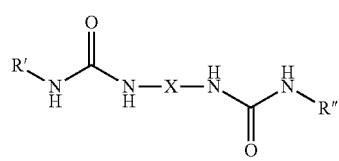

(I)

where
X is a branched alkyl bridge; and
R' and R" are alkyl groups.

In an embodiment, the branched alkyl bridge group is chosen to provide a desired viscosity suitable for ink-jet printing. The branched alkyl bridge group can include at least one methyl side group. In other embodiments, higher carbon branches can be used, such as ethyl or propyl branch groups. The branched alkyl bridge group can include any suitable number of carbon atoms that will provide the desired viscosity. For example, X can be a $C_3$ to $C_{15}$ branched alkyl bridge group, such as a $C_6$ to $C_{12}$ branched alkyl bridge group.

R' and R" can be any suitable alkyl group that will allow for the desired viscosity. The R' and R" substituents can be linear or branched, short or long chain alkyl groups. In an embodiment, the alkyl groups are selected from $C_1$ to $C_{10}$ alkyls that are linear, branched or cyclic, such as $C_3$ to $C_6$ or $C_8$ alkyls. Examples include methyl, ethyl, n-propyl, isopropyl, n-butyl, sec-butyl, tert-butyl, n-amyl, isoamyl, sec-amyl, tert-pentyl, neopentyl, 3-pentyl, n-hexyl, sec-hexyl, isohexyl, tert-hexyl. In an embodiment, the alkyls are selected from the group consisting of isoamyl, tert-pentyl, n-butyl, sec-butyl and n-propyl.

The viscosity of the amorphous component can be adjusted to any desired value based on the structure and length of the X alkyl bridge core and R' and R" substituents. For example, branching of the alkyl core structure may be used to tune the degree of amorphous character and to modulate viscosity of the amorphous components. As disclosed herein, it was recognized that the urea functional group with its strong hydrogen bonding capacity might provide prohibitively high viscosities and/or crystalline character. In accordance with embodiments disclosed herein, the branched alkyl core serves as a means to reduce viscosity and increase the amorphous character of the amorphous component.

In embodiments, the compound of formula I is further defined by formula II:

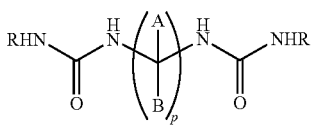

II wherein p is an integer from 4 to 6; and each occurrence of A and B are independently selected from the group consisting of hydrogen, methyl, and ethyl, provided that at least one occurrence of A or B is not hydrogen. In embodiments, A and B combine to provide at least 2 non-hydrogen groups, or at least 3 non-hydrogen groups, or at least 4 non-hydrogen groups.

In embodiments, in structures I or II each R may be isoamyl.

In embodiments, in structures I or II each R may be tert-pentyl.

In embodiments, in structures I or II each R may be n-butyl.

In embodiments, in structures I or II each R may be n-propyl.

In embodiments, in structures I or II each R may be sec-butyl.

In embodiments, the urea component comprises a branched alkyl core, wherein a degree of branching of the branched alkyl core is sufficient to provide the urea component as an amorphous structure. In embodiments, the branched alkyl core has 1, 2, 3, 4, 5, or more points of branching. The branching need not be ordered in any periodic manner, although for simplicity of preparation, where the branched alkyl core is constructed de novo, symmetry or regular structural features may facilitate synthesis. In some embodiments the urea component comprises two urea functional groups.

In an embodiment, a plurality of any of the amorphous bis-urea compounds of the present disclosure can be employed. In particular embodiments, the urea component comprises a compound of formula III:

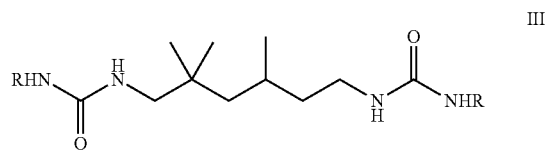

III and/or its 2,4,4 isomer:

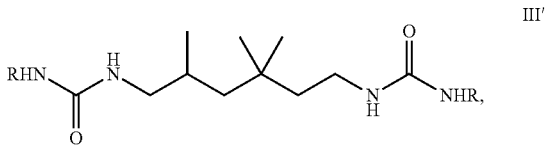

III' wherein each R is independently selected from a $C_1$ to $C_6$ branched or straight chain alkyl. In such embodiments, the branched alkyl core can be based on reaction of 2,2,4-trimethylhexanediisocyanate (TMHDI, typically commercially available as a mixtures of III and III') with an appropriate amine ($RNH_2$). In embodiments, each R is isoamyl. In other embodiments, each R is n—propyl. It will be appreciated by those skilled in the art that these exact compounds are merely exemplary and provide proof of concept for the ability to create amorphous bis-ureas and that such compounds are useful when formulated as the amorphous component of a phase change ink comprising a crystalline and amorphous component, in accordance with the Examples provided herein below.

Other branched alkyl cores may be employed in accordance with embodiments disclosed herein. In embodiments, a branched alkyl core may also embrace intervening cycloalkyl, i.e., cycloaliphatic groups, which may also be optionally substituted with methyl or ethyl groups. For example, in embodiments, the core of an amorphous component may be based on reaction of amines ($RNH_2$) with 4,4'-dicyclohexylmethane-diisocyanate, 3-isocyanatomethyl-3,5,5-trimethyl-cycohexylisocyanate (isophorone-based), and the like.

Example viscosity data as it varies with temperature for one of the amorphous bis-urea components, bis (isoamylamine)TMHDI urea, is shown in FIG. 1. Example viscosities can generally be above $1\times10^5$ cps at 40° C., such as $1\times10^6$ cps or higher, or $1.6\times10^6$ cps. Example viscosities can generally be below $1\times10^4$ cps at 140° C., such as viscosities ranging from about $5\times10^3$ cps to about $5\times10^2$ cps, or about $1\times10^3$ cps. In an example, the amorphous bis-urea component has a viscosity ranging from 100 cps to 6,000 cps at a temperature of 140° C., wherein the viscosity is a measure on a RFS3 controlled strain Rheometer from TA Instruments equipped with a Peltier heating plate and using a 25 mm parallel plate using a temperature sweep from high to low temperatures in temperature decrements of 5° C., a soak equilibration time of 120 seconds between each temperature and at a constant frequency of 1 Hz.

An important design criterion for using bis-ureas as amorphous resins is the selection of lower-viscosity materials (to enable jettable compositions). This can be achieved by using branched isocyanate cores and small molecule amines as building blocks. The final viscosity of the ink composition containing the amorphous component is much lower than the native viscosity of the amorphous component alone, and it is largely driven by the viscosity of the crystalline component, which is present in a higher ratio than the amorphous component. The ink can have any desired viscosity, such as, for example, a viscosity of 15 cps or less at a temperature of about 140° C., or a viscosity that is 12 cps or less at a temperature of about 140° C., such as a viscosity ranging from about 12 cps to about 4 cps.

In an embodiment, the amorphous materials have Tg's (glass transition temperatures) but do not exhibit crystallization and melting peaks by DSC (10° C./min from −50 to 200 to −50° C.). The $T_g$ values are typically from about −25 to about 50° C., or from about −10 to about 40° C., or from about −5 to about 35° C., to impart the desired toughness and flexibility to the inks. The selected amorphous materials have low molecular weights, such as less than 1000 g/mol, or from about 100 to about 1000 g/mol, or from about 200 to about 1000 g/mol, or from about 300 to about 1000 g/mol. Higher molecular weight amorphous materials such as polymers become viscous and sticky liquids at high temperatures, but have viscosities that are too high to be jettable with piezoelectric printheads at desirable temperatures. Suitable amorphous components disclosed herein are based on ureas having a branched alkyl core.

The amorphous compounds of the present disclosure can be made by any suitable method. One such method includes reacting a diisocyanate having a branched alkyl core with small molecule amines, as follows:

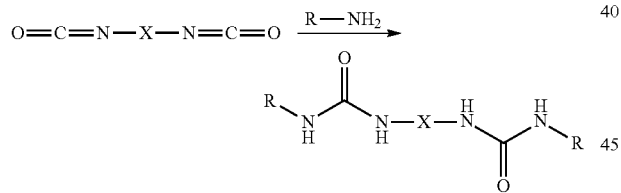

Suitable reaction temperatures and times may depend on the precise reactants employed and can be readily determined by one of ordinary skill in the art. This method is illustrated in more detail by the process of Example 1 below.

Phase Change Ink Composition

An embodiment of the present disclosure is directed to a phase change ink composition. The ink composition includes components comprising (a) an amorphous bis-urea component, including any of the amorphous bis-urea compounds described above, (b) a crystalline component, and (c) an optional colorant.

Crystalline Component

Any suitable crystalline compounds can be employed. The crystalline component in the ink formulation can drive the phase change through rapid crystallization on cooling. The crystalline component can also set up the structure of the final ink film and create a hard ink by reducing the tackiness of the amorphous component. The crystalline components exhibit crystallization, relatively low viscosity at the desired printer operating temperatures and relatively high viscosity at room temperature. Example viscosities can be greater than or equal to $10^1$ centipoise (cps), or from about 0.5 to about 10 cps, or from about 1 to about 10 cps at about 140° C. The relatively high viscosity at room temperature can be, for example, greater than $10^6$ cps.

Because the crystalline components dictate the phase change of the ink, rapid crystallization can allow immediate print processing, as may be desired for some applications, such as spreading, duplex printing, and so forth, and may also provide reduced showthrough on uncoated substrates.

By differential scanning calorimetry (DSC) (10° C./min from −50 to 200 to −50° C.), desirable crystalline components show sharp crystallization and melting peaks, and the ΔT between them can be, for example, less than 55° C. The melting point can be below the upper limit of the jetting temperature, such as below from about 150° C. to about 140° C. The melting point can be suitable for preventing or reducing blocking and print transfer upon standing at lower printer temperatures, such as may occur during printer standby modes. Examples of such low printer temperatures include temperatures up to 65° C. or more, such as about 66° C. or above about 67° C.

Examples of suitable crystalline materials include the following:

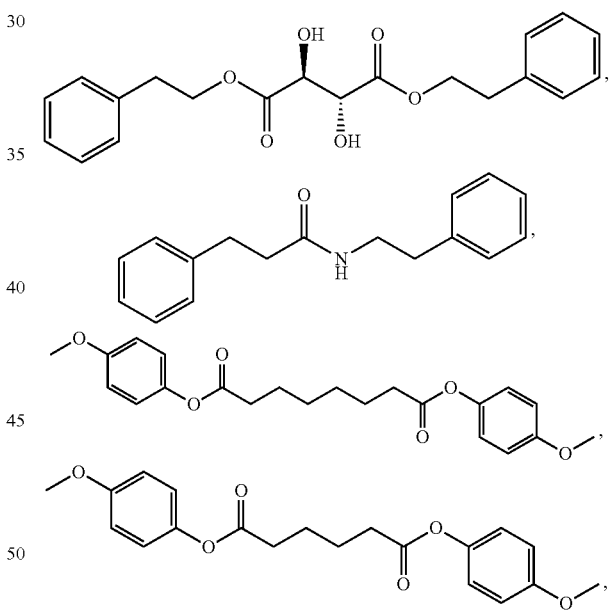

which are disclosed in U.S. Patent Application No. 2012/0274699, the disclosure of which is herein incorporated by reference in its entirety.

Other crystalline compounds that can be used include crystalline diamide compounds with an aromatic ring core, as disclosed in U.S. patent application Ser. No. 13/848,365, filed Mar. 21, 2013, the disclosure of which is incorporated herein by reference in its entirety. The diamide compounds can comprise any suitable aromatic ring core such as, for example, a benzene group or a naphthalene group. The ring structure can be substituted with organic amides at any suitable position that will provide the desired phase change properties for the ink, as illustrated by formula IV:

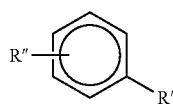

(IV)

where R' and R" are selected from organic amide groups that include at least one $C_1$ to $C_{40}$ substituent group. Examples of suitable R' and R" groups include those independently selected from the amide groups of formulae V and VI:

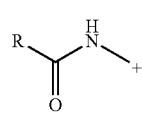

(V)

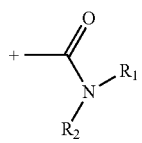

(VI)

where R, $R_1$ and $R_2$ can be independently selected from the group consisting of a hydrogen atom or a linear, branched or cyclic, saturated or unsaturated, aliphatic or aromatic $C_1$ to $C_{40}$ substituent group that will result in a crystalline compound that provides the desired ink properties, such as a liquid phase state with suitable viscosity at jetting temperatures and solid phase state at about room temperature (e.g., about 25° C.); and wherein at least one of R, $R_1$ and $R_2$ is not a hydrogen atom. In formulae V and VI, the single bond and "+" sign together represent the bond between the benzyl group of formula IV and either the nitrogen atom of formula V or the carbonyl group of formula VI.

Colorant

In an embodiment, the colorant employed in the inks of the present disclosure is chosen from a dye, a pigment or mixtures thereof. Any dye or pigment may be chosen, provided that it is capable of being dispersed or dissolved in the ink carrier and is compatible with the other ink components. Examples of suitable dyes and pigments are well known in the art.

Any other ingredients suitable for use in phase change inks can also optionally be included in the compositions of the present disclosure. One of ordinary skill in the art would readily be able to determine other ingredients that can be employed.

The colorant may be present in the phase change ink in any desired or effective amount to obtain the desired color or hue such as, for example, from about 0.1 percent by weight of the ink to about 50 percent by weight of the ink, or from about 0.2 percent by weight of the ink to about 20 percent by weight of the ink, or from about 0.5 percent by weight of the ink to about 10 percent by weight of the ink.

In embodiments, there are provided phase change ink compositions which comprise a blend of (1) crystalline and (2) amorphous components, generally in a weight ratio of from about 60:40 to about 95:5, respectively. In more specific embodiments, the weight ratio of the crystalline to amorphous component is from about 65:35 to about 95:5, or is from about 70:30 to about 90:10. In one embodiment, the weight ratio is 70:30 for the crystalline and amorphous components, respectively. In another embodiment, the weight ratio is 80:20 for the crystalline and amorphous components, respectively.

Methods of Printing

The present disclosure is also directed to a printing method. The method comprises providing an ink jet printing device comprising a phase change ink composition. The phase change ink composition can be in solid form and comprises (a) an amorphous bis-urea component, (b) a crystalline component, and (c) optionally a colorant. The amorphous bis-urea component can be any of the bis-urea compounds disclosed herein.

The solid phase change ink composition is heated to a temperature above the melting point of the phase change ink composition to liquefy the ink. The liquefied ink can then be jetted from the ink jet printing device onto a substrate to form an image. Any suitable printing device and/or technique for jetting the ink can be used, examples of which are well known in the art.

Any suitable substrate or recording sheet can be employed in the printing processes of the present disclosure. Examples of suitable substrates include plain papers such as XEROX® 4200 papers, XEROX® Image Series papers, Courtland 4024 DP paper, ruled notebook paper, bond paper, silica coated papers such as Sharp Company silica coated paper, JuJo paper, HAMMERMILL LASERPRINT paper, and the like, glossy coated papers such as XEROX® Digital Color Elite Gloss, Sappi Warren Papers LUSTROGLOSS, specialty papers such as Xerox® DURAPAPER, and the like, transparency materials, fabrics, textile products, plastics, polymeric films, inorganic recording mediums such as metals and wood, and the like.

The phrase "printing device" as used herein encompasses any apparatus, such as a digital copier, bookmaking machine, facsimile machine, multi-function machine, and the like, which performs a print outputting function for any purpose.

EXAMPLES

The present disclosure provides the following examples of novel amorphous bis-urea materials which are suitable for phase-change solid ink. The bis-ureas were prepared by reaction of TMHDI (an isomeric mixture of 2,4,4'- and 2,2',4-trimethyl hexamethylenediisocyanate, available from Evonik corporation as "VESTANAT TMDI") with various amines. The bis-ureas were then mixed with a crystalline material, N-phenylethyl benzamide ("PEB"), and the resulting ink was printed on coated paper by K-proof. The print samples demonstrated improved robustness with respect to scratch, fold, and fold offset compared to some other known phase-change inks. The ink described in the examples was shown to surpass the rub resistance of the other known phase-change inks.

TMHDI was reacted with 2 equivalents of amine to make the bis-ureas described below in Examples 1A to 1E.

Synthesis of Amorphous Bis(Propylamine)TMHDI Bis-Ureas

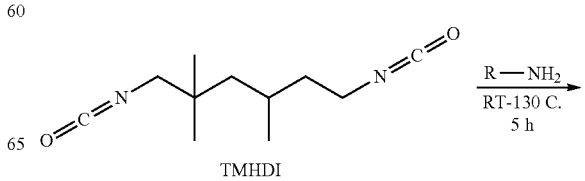

TMHDI

-continued

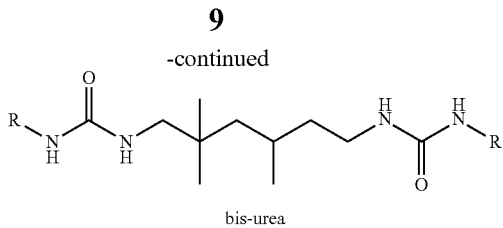

bis-urea

Example 1A

Bis Urea Synthesis Using Isoamylamine, R=CH$_2$CH$_2$(CH$_3$)$_2$

To a 16 oz. jar equipped with magnetic stir was charged 40 g isoamylamine (MW=87, 0.46 moles). With stirring at room temperature 50.7 g TMHDI (MW=210, 0.24 moles, 1.05% excess) was slowly added dropwise, so as to maintain the temperature below the boiling point of the amine material. After the addition was completed, the mixture was heated in a 130° C. using an oil bath for one hour. A small sample was taken to run IR. It showed a small isocyanate peak caused by excess of TMHDI. A small amount of butanol was added to react with the excess TMHDI. This was to ensure that no excess amine was left. IR was checked again to show that no isocyante remained.

Example 1B

Bis Urea Synthesis Using Tert-Pentylamine, R=CH$_2$C(CH$_3$)$_2$CH$_3$

Bis Urea was prepared in a similar fashion as set forth in Example 1A, except the amine used was tert-pentylamine.

Example 1C

Bis Urea Synthesis Using n-Butylamine R=C$_4$H$_9$

Bis Urea was prepared in a similar fashion as set forth in Example 1A, except the amine used was n-butylamine and toluene was added as a co-solvent due to the volatility of the amine. The toluene was removed by vacuum distillation once the reaction was complete.

Example 1D

Bis Urea Synthesis Using n-Propylamine, R=C$_3$H$_7$

Bis Urea was prepared in a similar fashion as set forth in Example 1A, except the amine used was n-propylamine.

Example 1E

Bis Urea Synthesis Using Sec-Butylamine R=C$_4$H$_9$

Bis Urea was prepared in a similar fashion as set forth in Example 1A, except the amine used was sec-butylamine.

Materials Properties

Figure 2:
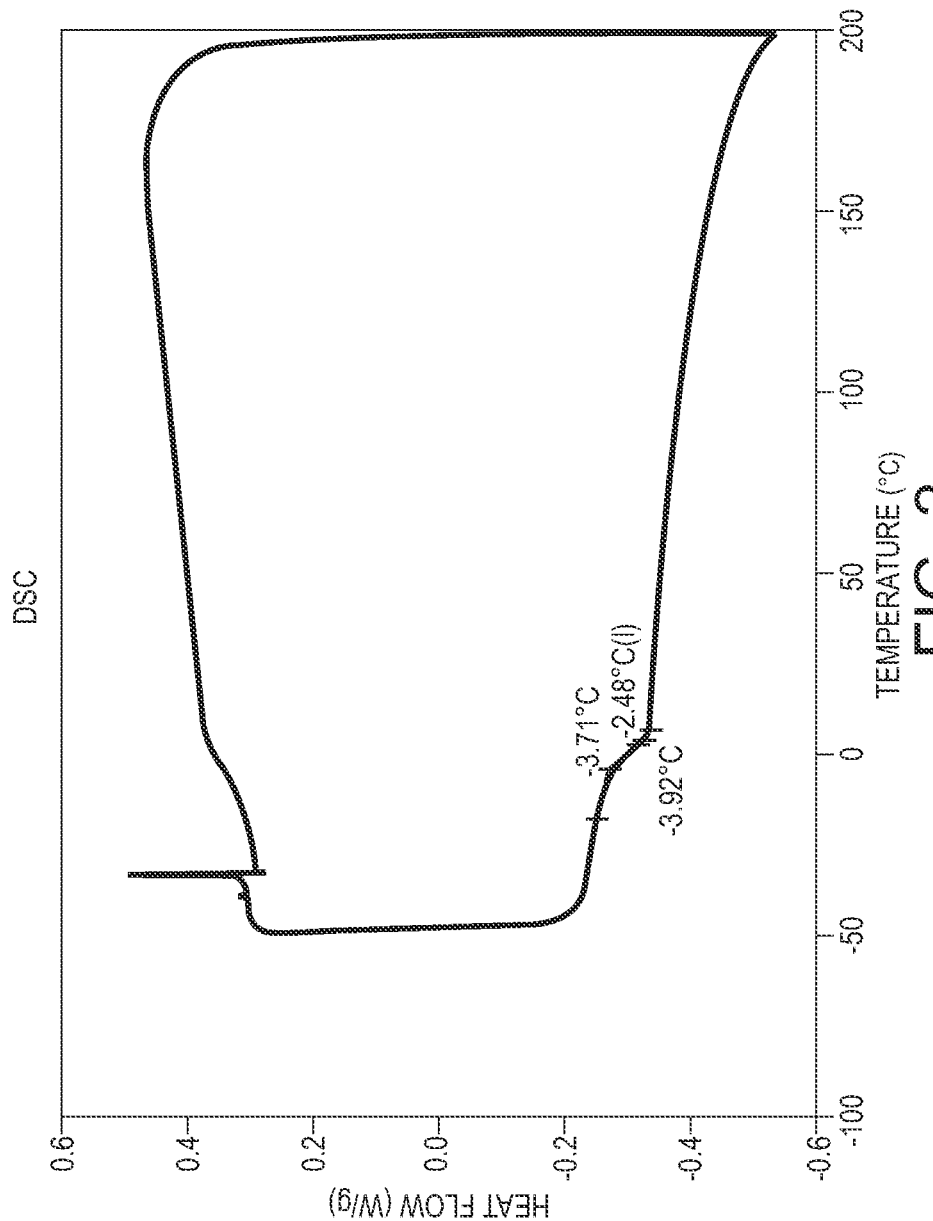

Viscosity testing and differential scanning calorimetry ("DCS") was performed for the materials of Examples 1A to 1E. FIGS. 1 and 2 show viscosity and heat flow data that was collected. The rheology trace is consistent with an amorphous compound, and DSC showed a T$_g$ (glass transition temperature) of 2.48° C. Table 1 summarizes the characterization all of the amorphous bis-urea resins prepared.

TABLE 1

Summary of amorphous bis-urea resin properties

| Example | R | Tg/° C.* | Viscosity** @ 140° C. (cps) |
|---|---|---|---|
| 1A | isoamyl | 2.48 | 907 |
| 1B | tert-pentyl | 28.4 | 5,119 |
| 1C | n-butyl | −12.07 | 276 |
| 1D | n-propyl | 6.23 | 222 |
| 1E | sec-butyl | 15.3 | 1448 |

*The samples were measured on a Q1000 Differential Scanning Calorimeter (TA Instruments) at a rate of 10° C./min from −50° C. to 200° C. to −50° C.; midpoint values are quoted.
**The samples were measured on a RFS3 controlled strain Rheometer (TA instruments) equipped with a Peltier heating plate and using a 25 mm parallel plate. The method used was a temperature sweep from high to low temperatures, in temperature decrements of 5° C., a soak (equilibration) time of 120 seconds between each temperature and at a constant frequency of 1 Hz.

Ink Formulations

Five Inks containing amorphous bis-ureas were prepared using N-phenylethylbenzamide (N-PEB) as the crystalline material and Cyan pigment dispersion in TBCT vehicle. The formulations are summarized below

| Component | wt % | m (g) |
|---|---|---|
| Ink Formulation #1 | | |
| N-phenylethyl benzamide (N-PEB crystalline) | 76.46 | 3.82 |
| (isoamylamine)$_2$-TMHDI | 10.14 | 0.51 |
| Pigment concentrate (HOSTAPERM ® Blue (commercially available from Clariant)/TBCT | 13.4 | 0.67 |
| TOTAL | 100.00 | 5.0 |
| Ink Formulation #2 | | |
| N-phenylethyl benzamide (N-PEB crystalline) | 76.46 | 3.82 |

-continued

| Component | wt % | m (g) |
|---|---|---|
| (t-pentylamine)₂-TMHDI | 10.14 | 0.51 |
| Pigment concentrate (HOSTAPERM ® Blue)/TBCT | 13.4 | 0.67 |
| TOTAL | 100.00 | 5.0 |

Ink Formulation #3

| Component | wt % | m (g) |
|---|---|---|
| N-phenylethyl benzamide (N-PEB crystalline) | 76.46 | 3.82 |
| (butylamine)₂-TMHDI | 10.14 | 0.51 |
| Pigment concentrate (HOSTAPERM ® Blue)/TBCT | 13.4 | 0.67 |
| TOTAL | 100.00 | 5.0 |

Ink Formulation #4

| Component | wt % | m (g) |
|---|---|---|
| N-phenylethyl benzamide (N-PEB crystalline) | 76.46 | 3.82 |
| (propylamine)₂-TMHDI | 10.14 | 0.51 |
| Pigment concentrate (HOSTAPERM ® Blue)/TBCT | 13.4 | 0.67 |
| TOTAL | 100.00 | 5.0 |

Ink Formulation #5

| Component | wt % | m (g) |
|---|---|---|
| N-phenylethyl benzamide (N-PEB crystalline) | 76.46 | 3.82 |
| (sec-butylamine)₂-TMHDI | 10.14 | 0.51 |
| Pigment concentrate (HOSTAPERM ® Blue)/TBCT | 13.4 | 0.67 |
| TOTAL | 100.00 | 5.0 |

Ink Properties

Figure 3:
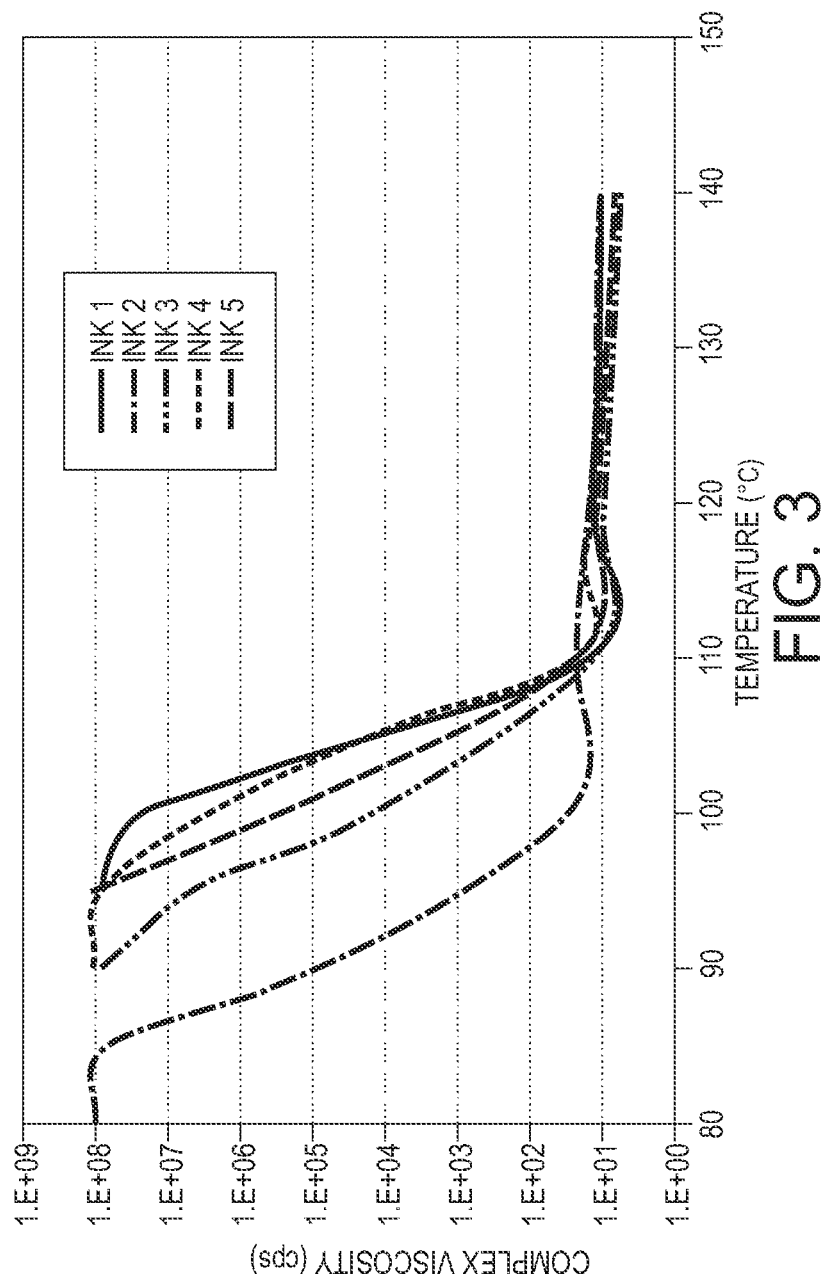
FIG. 3 shows ink rheology measured for five ink formulations containing amorphous bis-ureas, according to an example of the present disclosure.

Ink rheology was measured for all five inks, as shown in FIG. 3. Table 2 shows that all five tested ink formulations have the appropriate viscosity at 140° C. for jetting (about 10 cps). Typically urea compounds are very viscous owing to their extended hydrogen bonding. By correct design of the molecule (e.g., branched trimethylhexyl core), miscibility was enhanced with the crystalline component, and the hydrogen bonding was counter-balanced to enable reduced viscosity. Conversely, linear core chain bis-urea molecules are high melting, crystalline compounds.

TABLE 2

Summary of Ink Viscosities

| Ink # | Viscosity @ 140° C. (cps) |
|---|---|
| 1 | 6.67 |
| 2 | 10.7 |
| 3 | 5.78 |
| 4 | 9.7 |
| 5 | 6.96 |

Robustness Tests

To test robustness of prints, ink formulations 1, 2, and 3 were printed onto Xerox® Digital Color Elite Gloss, 120 gsm (DCEG) coated papers using a K-proofer gravure printing plate, which is rigged with a pressure roll set at low pressure. The gravure plate temperature was set at 142° C., but the actual plate temperature is about 134° C. The K-proofer apparatus (manufactured by RK Print Coat Instrument Ltd., Litlington, Royston, Heris, SG8 0OZ, U.K.) is a useful printing tool to screen a variety of inks at small scale and to assess image quality on various substrates. The inks gave robust images that could not be easily removed from the substrates. When a metal tip with a curved tip at an angle of about 15° from vertical, with a weight of 528 g applied, was drawn across the image at a rate of approximately 13 mm/s no ink was visibly removed from the image. The tip is similar to a lathe round nose cutting bit with radius of curvature of approximately 12 mm. Inks 1 and 4 showed better robustness than some commercially available phase-change inks in terms of scratch, fold crease, and fold offset.

Print Characterization

Ink 1 was scaled up to 175 g scale and printed. The example ink formulations were printed, and compared to control inks that do not contain the amorphous urea component. Robustness tests of prints using the procedure described above show that the example ink formulations show breakthrough performance in rub resistance, which is a key metric for ink finishing requirements in the field.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein.

While the present teachings have been illustrated with respect to one or more implementations, alterations and/or modifications can be made to the illustrated examples without departing from the spirit and scope of the appended claims. In addition, while a particular feature of the present teachings may have been disclosed with respect to only one of several implementations, such feature may be combined with one or more other features of the other implementations as may be desired and advantageous for any given or particular function. Furthermore, to the extent that the terms "including," "includes," "having," "has," "with," or variants thereof are used in either the detailed description and the claims, such terms are intended to be inclusive in a manner similar to the term "comprising." Further, in the discussion and claims herein, the term "about" indicates that the value listed may be somewhat altered, as long as the alteration does not result in nonconformance of the process or structure to the illustrated embodiment. Finally, "exemplary" indicates the description is used as an example, rather than implying that it is an ideal.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompasses by the following claims.

What is claimed is:

1. An amorphous bis-urea compound of formula I:

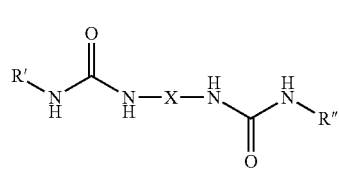

(I)

where
X is a branched alkyl bridge; and
R' and R" are alkyl groups.

2. The compound of claim 1, wherein the branched alkyl bridge includes at least one methyl group.

3. The compound of claim 1, wherein X is a $C_3$ to $C_{15}$ branched alkyl bridge group.

4. The compound of claim 3 wherein R' and R" are $C_1$ to $C_{10}$ alkyls.

5. The compound of claim 4, wherein R' and R" are selected from the group consisting of methyl, ethyl, n-propyl, isopropyl, n-butyl, sec-butyl, tert-butyl, n-amyl, isoamyl, sec-amyl, tert-pentyl, neopentyl, 3-pentyl, n-hexyl, sec-hexyl, isohexyl and tert-hexyl.

6. The compound of claim 4, wherein the amorphous bis-urea component has a viscosity ranging from 100 cps to 6,000 cps at a temperature of 140° C., wherein the viscosity is measure on a RFS3 controlled strain Rheometer from TA Instruments equipped with a Peltier heating plate and using a 25 mm parallel plate using a temperature sweep from high to low temperatures in temperature decrements of 5° C., a soak equilibration time of 120 seconds between each temperature and at a constant frequency of 1 Hz.

7. The compound of claim 1, wherein R' and R" are $C_1$ to $C_{10}$ alkyls.

8. The compound of claim 1, wherein the amorphous bis-urea compound is selected from the group consisting of:

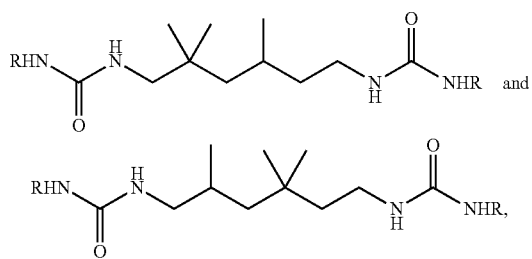

where R is a $C_1$ to $C_6$ branched or straight chain alkyl.

9. A method comprising:
providing an ink jet printing device including a phase change ink composition, the phase change ink composition being in solid form and comprising (a) a crystalline component, (b) an amorphous bis-urea component, and (c) optionally a colorant, the amorphous bis-urea component being a compound of formula I:

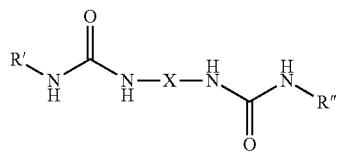

where
X is a branched alkyl bridge; and
R' and R" are alkyl groups;
heating the solid phase change ink composition to a temperature above the melting point of the composition to liquefy the ink composition; and
jetting the liquefied ink composition from the ink jet printing device onto a substrate to form an image.

10. The method of claim 9, wherein the branched alkyl bridge includes at least one methyl group.

11. The method of claim 9, wherein X is a $C_3$ to $C_{15}$ branched alkyl bridge group.

12. The method of claim 9, wherein R' and R" are $C_1$ to $C_{10}$ alkyls.

13. The method of claim 9, wherein the amorphous bis-urea component comprises at least one compound selected from the group consisting of:

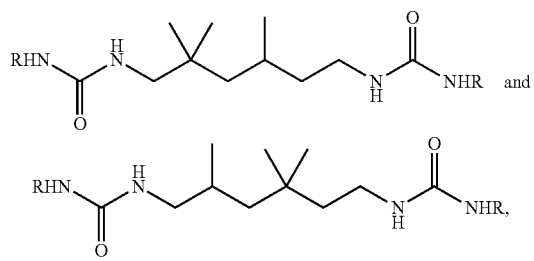

where R is a $C_1$ to $C_6$ branched or straight chain alkyl.

14. The method of claim 9, wherein R' and R" are selected from the group consisting of methyl, ethyl, n-propyl, isopropyl, n-butyl, sec-butyl, tert-butyl, n-amyl, isoamyl, sec-amyl, tert-pentyl, neopentyl, 3-pentyl, n-hexyl, sec-hexyl, isohexyl and tert-hexyl.

15. The method of claim 9, wherein the ink containing the amorphous bis-urea component has a viscosity less than 15 cps at a temperature of 140° C.

16. A phase change ink composition, comprising:
a crystalline component;
an amorphous bis-urea component having a compound of formula 1:

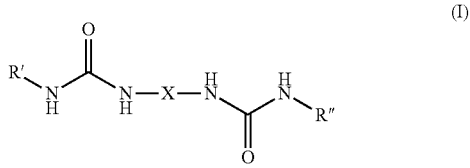

where
X is a branched alkyl bridge; and
R' and R" are alkyl groups; and
optionally a colorant,
wherein the ink containing the amorphous bis-urea component has a viscosity less than 15 cps at a temperature of about 140° C.

17. The composition of claim 16, wherein the branched alkyl bridge includes at least one methyl group.

18. The composition of claim 16, wherein X is a $C_3$ to $C_{15}$ branched alkyl bridge group.

19. The composition of claim 16, wherein R' and R" are $C_1$ to $C_{10}$ alkyls.

20. The composition of claim 16, where the ratio of crystalline component to amorphous bis urea component is 60:40 to 95:5 crystalline:amorphous.

* * * * *